United States Patent [19]

Kapuscinski et al.

[11] Patent Number: 4,801,550
[45] Date of Patent: Jan. 31, 1989

[54] METHOD FOR SEPARATING AND ANALYZING NUCLEIC ACIDS

[75] Inventors: Jan Kapuscinski, Carmel; Zbigniew Darzynkiewicz, Chappaqua, both of N.Y.

[73] Assignee: Sloan-Kettering Institute for Cancer Research, New York, N.Y.

[21] Appl. No.: 613,156

[22] Filed: May 23, 1984

[51] Int. Cl.$^4$ .................. G01N 31/02; G01N 33/50
[52] U.S. Cl. .................. 436/94; 210/709; 210/745; 436/178; 536/27; 536/28; 536/29
[58] Field of Search .................. 210/709, 745; 436/94, 436/178, 909; 536/27–29; 260/112 R

[56] References Cited

U.S. PATENT DOCUMENTS

| | | | |
|---|---|---|---|
| 3,157,637 | 11/1964 | Khym | 536/29 X |
| 4,168,262 | 9/1979 | Kinsella et al. | 260/112 R |
| 4,348,479 | 9/1982 | Kinsella et al. | 260/112 R X |
| 4,427,580 | 1/1984 | Kinsella et al. | 260/112 R |
| 4,482,482 | 11/1984 | Haff et al. | 260/112 R |
| 4,623,723 | 11/1986 | Keller et al. | 536/28 X |

OTHER PUBLICATIONS

Kapuscinski et al., Biochemical Pharmacology, vol. 30, 1981, pp. 231–240.
Darzynkiewicz et al., Chemical Abstracts, vol. 100, 1983, No. 100:2850s.
Kapuscinski et al., Chemical Abstracts, vol. 96, 1982, No. 96:212697q.
Kapuscinski et al., Chemical Abstracts, vol. 95, 1981, No. 95:18009f.
Nag et al., Chemical Abstracts, vol. 101, 1983, No. 101:126186n.
Ballamy et al., Chemical Abstracts, vol. 88, 1975, No. 88:117537p.
Reitz et al., Chemical Abstracts, vol. 77, 1972, No. 161480m.
Berne et al., Dynamic Light Scattering, Wiley, NY(1976) 164–198.
Wilson et al., Biochemistry, vol. 18, 1979, pp. 2192–2196.
Darzynkiewicz et al., Experimental Cell Research 148 (1983) 31–46.
Kapuscinski et al., Nucleic Acid Research, vol. 11, No. 21, 1983, pp. 7555–7568.
Kapuscinski et al., Biochemical Pharmacology, vol. 32, No. 24, pp. 3679–3694, 1983.
Kapuscinski et al., Journal of Biomolecular Structure and Dynamics, vol. 1, Issue Number VI(1984), pp. 1485–1499.
Bradley et al., Molecular Associations in Biology, Paris May8–11, 1967, pp. 261–270.
Kapuscinski et al., Cytology, vol. 2, No. 4, 1982, pp. 201–211.
Kapuscinski et al., Proc. Natl. Acad. Sci. USA 81, pp. 7368–7372, 1984.

Primary Examiner—Benoit Castel
Assistant Examiner—Robert J. Hill, Jr.
Attorney, Agent, or Firm—John P. White

[57] ABSTRACT

The primary and/or secondary structure of nucleic acid as well as its content and molecular weight can be analyzed in solutions by light scatter or fluorescence measurements after treatment with 3 or 4 ring aromatic cations which bind to single-stranded nucleic acids by cooperative association and induce their condensation (collapse). Preparative separation of nucleic acids of different types from the mixtures in the solution is also accomplished by the same principle and techniques wherein each condensed acid is removed from solution and the condensation reversed.

5 Claims, 2 Drawing Sheets $d(Is/Io)/d([AO])$

AO CONCENTRATION [μM]

METHOD FOR SEPARATING AND ANALYZING NUCLEIC ACIDS

This invention was made with Government support under CA 23296 and CA 28704 awarded by DHHS. The Government has certain rights in this invention.

BACKGROUND OF THE INVENTION

The present invention is concerned with the measurement or analysis of the primary and/or secondary structure of nucleic acids as well as the concentration, type and molecular weight thereof. The invention also provides a method for the separation and recovery of various nucleic acids from a mixture thereof in solution.

Known methods for analysis include UV, CD or fluorescence spectroscopy. These methods, however, often are complex and require decomposition of the polymer and/or the use of chromatography. Decomposition of the polymer, if required, precludes simple recovery. Furthermore, the known methods measure only one property at a time.

The inventive method utilizes precipitation of nucleic acids. Interactions between aromatic cations and nucleic acids at high binding density and high concentration of the ligand are known to often result in the precipitation of the product. Although this phenomenon was observed earlier (Kapuscinski et al Cytometry 2 201-211 (1982) and references cited therein), the conditions of the precipitate formation were not studied in detail and no attempt was made to characterize the molecular structure of these complexes. Rather, the precipitation was treated as a hindrance in the titration experiments which were normally analyzed by spectroscopic techniques and the titrations were usually terminated when precipitation occured.

SUMMARY OF THE INVENTION

Using precipitation techniques, the present invention provides a method for the separation, recovery and analysis of nucleic acids.

The primary and/or secondary structure of a nucleic acid as well as its content and molecular weight can be analyzed in solutions by light scatter or fluorescence measurements after treatment with 3- or 4-ring aromatic cations which bind the single-stranded nucleic acid by cooperative association and induces condensation (collapse) of the nucleic acid.

More specifically, solutions can be analyzed for the quantity (concentration) of nucleic acids in solution, the type of nucleic acids in solution (ribo- or deoxyribonucleic acid), the primary structure of nucleic acids in solution (base composition of the homopolymers or double-stranded copolymers, the secondary structure of nucleic acids in solution (discrimination between single- vs double-stranded forms), and the molecular weight of nucleic acids in solution.

This principle can also be used in preparative techniques for the separation of nucleic acids of different types from mixtures thereof in solution. The precipitates are recovered and the precipitation reaction reversed.

BRIEF DESCRIPTION OF THE DRAWINGS

In the Drawings FIGS. 1 A-C show light scatter changes during titration of poly(rU) with DHAQ.

FIG. 1 B shows the derivative of the light-scatter transition profiles of the transitions as presented in FIG. 1 A.

FIG. 1 C shows the correlation between the poly(rU) concentration in the sample and the numerically integrated area S under the derivative of the light-scatter transition profiles shown in FIG. 1 B.

FIGS. 2 A-C show the derivative light scatter profiles representing a collapse of the nucleic acid structure during titration with acridine orange (AO) wherein:

FIG. 2 A shows the titration of homoribo-(solid line) and homodeoxyribopolymers (broken line). Maxima from left to right represent: Poly(rA), poly(rC), poly(rG), poly(dA), poly(rU) and poly(dU). All polymers were at $5 \pm 1 \times 10^{-6}$M (phosphates) concentrations. The profiles were normalized to 1 (arbitrary unit).

FIG. 2 B shows the titration of RNA (broken line) and calf thymus DNA (solid line) with AO. From left to right the maxima represent: rRNA (16S+23S), MS2RNA, thermally denatured (10 min in 100° C. then rapidly cooled in ice) and native (sonicated, MW approx. $3 \times 10^5$) DNA. Nucleic acids were at $10 \pm 1.5 \times 10^{-6}$M (phosphate) concentration. The profiles were normalized to 1 (arbitrary unit).

FIG. 2 C shows the titration of the mixture of denatured ($5.0 \times 10^{-6}$M) and native calf thymus DNA ($4.7 \times 10^{-6}$M). The area under the larger peak (which can be related to denatured DNA, see FIG. 2 B) is approximately twice as large as that under the smaller peak (representing native DNA).

DETAILED DESCRIPTION OF THE INVENTION

Figure 1A:
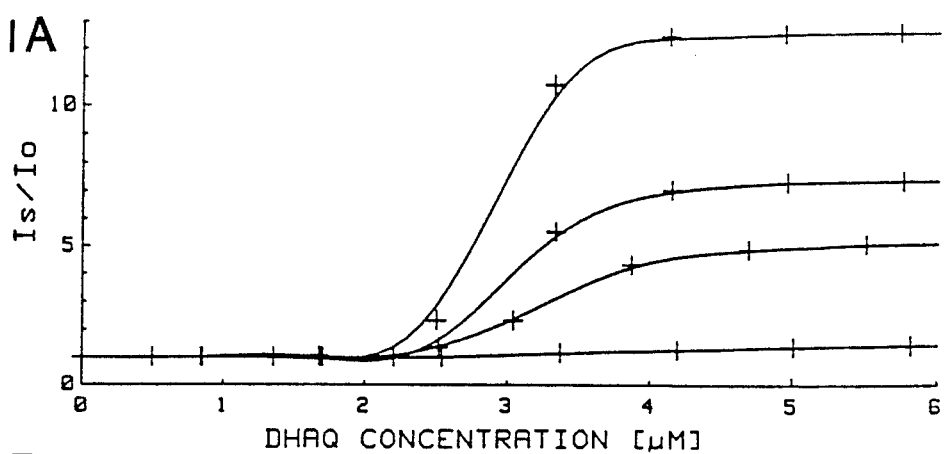
FIG. 1 A shows the light scatter (measured at 350 nm and 90° geometry) transition profiles representing condensation of the polymer. Concentrations of the polymer were 1.8, 7.3, 10.1 and $19.1 \times 10^{-7}$M (phosphate) from bottom to top, respectively. The results are expressed as relative light-scatter intensity Is/Io, where Is represents the intensity of the light scatter by the sample and Io represents initial intensity scatter by the blank sample (no ligand added).

During the past several years we have studied interactions between such ligands as 3,6-bis(dimethylamino) acridine (acridine orange, AO) or the new antitumor drug 1,4-dihydroxy-5,8-bis [2-[(2-hydroxyethyl)amino]ethylamino]-9,10-anthracenedione (DHAQ) and nucleic acids under conditions wherein the products are not soluble in aqueous media and undergo precipitation (Kapuscinski et al (supra); Kapuscinski et al Biochem. Pharm. 30, 231-240 (1981); Darzynkiewicz et at Exp.Cell Res. 148, 31-46 (1983); Kapuscinski et al Pharmacol. 32, 3679-3694 (1983); Kapuscinski and Darzynkiewicz Nucleic Acids Res. 11, 7555-7568 (1983)). Molecular mechanisms responsible for the precipitation will be discussed later. The stage preceding the precipitation, the condensation (collapse) of the polymer, can be conveniently and accurately monitored by light-scatter measurements. Namely, during the titration of nucleic acids with such ligands, the condensation of the polymer can be represented in the form of highly reproducible light-scatter transition curves. The transitions are cooperative and occur at narrow, well-defined concentrations of the ligands. Most importantly, the transitions that take place at specific concentrations of the ligands and, different and dependent upon: (a) the type of ligand; (b) the base composition of the nucleic acid; (c) whether the polymer is in single- or double-stranded conformation; and (d) whether the nucleic acid is of the ribo- or deoxyribo-type. The quantity (concentration)

or molecular weight of the nucleic acid also can be estimated from these curves. Analogous to the light-scatter changes, changes in luminescence of these complexes may also be observed if the ligand is a fluorochrome.

Thus a simple measurement of the light-scatter (or fluorescence) changes of nucleic acids in solutions can be seen to reflect their condensation after binding the cationic ligand, and thereby offers a novel approach for analyzing the primary and/or secondary structure of these polymers.

The inventive method can be used to analyze:

(1) The quantity (concentration) of nucleic acids in solution;

(2) the types of nucleic acids in solution (ribo- or deoxyribonucleic acid);

(3) the primary structure of nucleic acids in solution (base composition of the homopolymers or double-stranded copolymers);

(4) the secondary structure of nucleic acids in solution (discrimination between single- vs double-stranded forms); and (5) the molecular weight of nucleic acids in solution.

Although several physicochemical methods, such as UV, CD or fluorescence spectroscopy, can be applied to analyze the above properties of nucleic acids, the inventive method offers advantages and may complement the traditional techniques. First of all the inventive method is simple and versatile. It allows the measurement of several of the above-listed properties at the same time, whereas most of the traditional methods can measure only one feature at a time. Furthermore, the base composition analysis requires neither decomposition of the polymer nor chromatography. Also, discrimination of double- vs single-stranded polymer does not require separation of the mixture by affinity chromatography, gel electrophoresis or high speed centrifugation. Although the molecular weight of the polymers can be determined by light-scatter measurements (Berne and Pecora, Dynamic Light Scattering, Wiley, NY (1976) 164-198), the invention is based on the ligand-induced condensation of the polymer (the form factor increases by several orders of magnitude after transition from a Gausian chain to a sphere (Berne and Pecora, supra; Wilson and Bloomfield Biochem. 18 2192 -2196 (1979)) and this contributes to its novelty. Similar condensation can be induced by inorganic or nonaromatic organic polyvalent cations. In contrast to the invention method, however, these cations bind to the polymer exclusively by electrostatic forces, and this cannot be as specific for different types of nucleic acids, especially in relation to base composition, as the inventive method.

In general, the invention is a simple, rapid method that has sensitivity comparable to fluorescent spectroscopy, but in contrast to the latter is not limited to fluorescent ligands. Any commercial instrument which can measure light scatter in solutions (e.g. fluorimeter) can be used. Most preferable would be a dedicated instrument combining light-scatter measurements with automated titration in static- or in flow-channels. However we have not constructed one at this time.

A variety of ligands with different specificity towards different types of nucleic acids can be used. The sensitivity of discrimination between particular nucleic acid types varies depending on the ligand. 3- or 4-ring aromatic cations which bind to single stranded nucleic acids by cooperative association and induce their collapse are used to titrate the nucleic acids. Low cost and ready availability make acridine orange (AO) a highly preferred choice. However, many other ligands can also be used, e.g. DHAQ, Pyronine Y (Tetramethyldiamino xanthenyl chloride), Doxorubicin.HCl (Adriamycin), Proflavine. 2HCl (3,6-diamino acridine hydrochloride), DAPI (4,6-diamidino-) (4',2-phenylindole.2HCl), Ellipticine (5,11-dimethyl-6H-pyrido [4,3-b]carbazole), and crystal violet (Hexamethylpararosaniline.HCl).

The principle of nucleic acid discrimination which forms the basis of the invention is also applicable to preparative techniques for the physical separation of nucleic acids of different types. More specifically, in the course of a titration of two or more nucleic acid types, upon precipitation of one of the nucleic acids, the precipitate can be removed (e.g. by filtration or centrifugation) and the nucleic acid recovered from the precipitate, e.g. by ion-exchange columns, after dissolving the precipitate in organic solvents, as described in Kapuscinski et al., (Cytometry, supra). According to this procedure, the precipitate is solubilized in a buffer containing 25% (v/v) of ethanol and passed through a short column filled with a cation exchange resin which retains the ligand. Almost any cation exchange resin can be used. Although some will be more effective than others, the amount of cation to be removed is small and ion exchange resin efficiency is not a big factor for operability. Preferred ion exchange resins are the strongly acidic types such as the AG 50 or 50W series (T.M.) available from the BIORAD company. These have a cross-linked polystyrene gel (phenyl—$SO_3^-$) active polymer lattice with varying amounts of cross-linkage and particle size. However, as noted above, the efficiency of the ion exchange resin is a small factor. The sodium ion form of the AG50W-X8 TM designated material has provided good results. Also, Dowex A650W-X8 (equivalent product with Dow-Corning Trademark) is suitable. The X8 designation refers to approximately 8% cross-linking of the polymer forming the ion exchange resin.

EXPERIMENTAL

Nucleic acids in buffer solutions at a concentration of approximately $10^{-6}M$ (phosphates), or less, are treated with an increasing concentration of the ligand (titrated) and the collapse (condensation) of the polymer is monitored by scatter measurements. The pH of the buffer solutions may vary depending on the pKa of the ligand to assure that both the nucleic acid and the ligand are in ionic form. The reaction also depends on the ionic strength of the solution. Thus, different salt concentrations (e.g., NaCl) may be used in the buffer. The reaction is also temperature-dependent. The transition occurs at lower-ligand concentrations at lower temperatures. In the examples presented in this application the reaction was done in a buffer containing 5 mM Hepes, 150 mM NaCl, 1 mM EDTA, at pH 7.0, 25° C., but other buffers can also be used. Agents which protect the condensed polymer particles against extensive agglomeration, such as detergents (e.g., Triton X-100), also can be used.

Figure 1B:
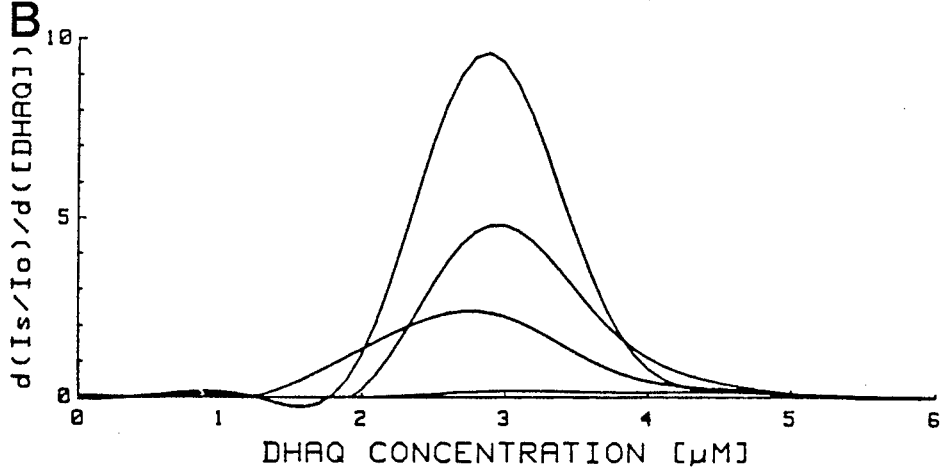
Figure 1C:
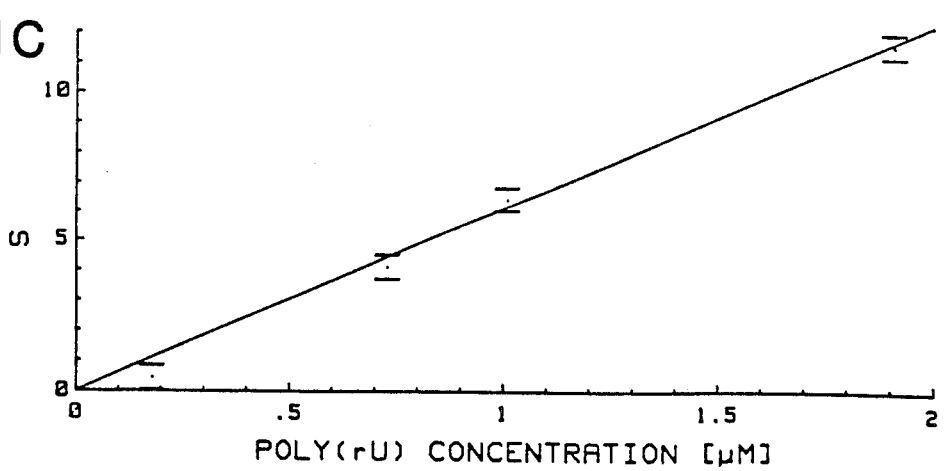

During the titration the intensity of the light scatter is measured at 90° geometry although other angles can also be used. Light at different wavelengths may be used. The optimal wavelength is that at which both the ligand and polymer have high transmittance. This minimizes the background. The light-scatter measurements may be expressed in several ways, such as arbitrary units, ratio to the initial scatter of the sample (Is/Io) (FIG. 1A) or in relation to another standard. The most convenient way is to present the results in the form of the plot of the first derivative of the scatter d(Is/Io)/dL vs the total ligand concentration (L), as shown in FIG. 1B. The integrated area under the derivative curve is proportional to the concentration of the studied polymer (FIG. 1C).

The critical free-ligand concentration, i.e., the free concentration of the ligand at equilibrium with the complex during the transition, depends on the polymer base or sugar composition (primary structure) and conformation (secondary structure). At the midpoint of the transition the critical free-ligand concentration ($L_c$) is independent of the polymer concentration. At that point $L_c = L_m - L_b$, where $L_m$ is the total ligand concentration at the midpoint of the transition and $L_b$ is the concentration of the bound ligand at the midpoint. $L_b$ can be estimated from the known concentration of the polymer and the known stoichiometry of the interaction between the nucleic acid and the ligand. Examples of such a calculation are shown in this application (Example 3). The value of $L_c$ is characteristic of the composition and secondary structure of the polymer. Acridine orange was used as the ligand in part because of its low cost and availability. When acridine orange was used as the ligand, the $L_c$ of ss (single stranded) ribopolymers was significantly lower than the $L_c$ of ss deoxyribopolymers (e.g., poly(rA) and poly(rU) vs poly (dA) and poly(dU), see FIG. 2A), the $L_c$ of ds (double stranded) ribopolymers was lower than that of ds deoxyribopolymers and, in general, the $L_c$ of ss polymers was lower than that of the ds polymers, of the same type.

Because the intensity of the scattered light is related to the number of the scatterers (Berni and Pecora supra), it is possible to estimate the molecular weight of the polymer from the light intensity using an appropriate standard and knowing the concentration of nucleic acid (P) in solution, as shown in Example 5.

EXAMPLE 1

Quantitative Estimate of Poly(rU)

The quantity of poly(rU) in solution can be estimated based on the comparison of the titration data of the sample containing an unknown concentration of the polymer with the appropriate calibration curve, as presented in FIG. 1C. This curve was derived from an experiment in which 2.5 ml aliquots of poly(rU) (dissolved in 0.15M NaCl, 5 mM Hepes, 1 mM EDTA, pH 7.0, and diluted to the desired final concentration as shown) were titrated with DHAQ at 25±0.1° C. Right-angle light scatter at 350 nm was measured for each point of the titration and the data expressed as the ratio Is/Io, where Is=intensity of the light scatter by the sample and Io=initial intensity of the light scatter by the sample (no ligand added).

The results were processed by a computer (interpolation, smoothing and derivation) and drawn by a digital plotter.

EXAMPLE 2

Identification of the Type (Ribo- vs Deoxyribo-) of Nucleic Acids

Figure 2A:
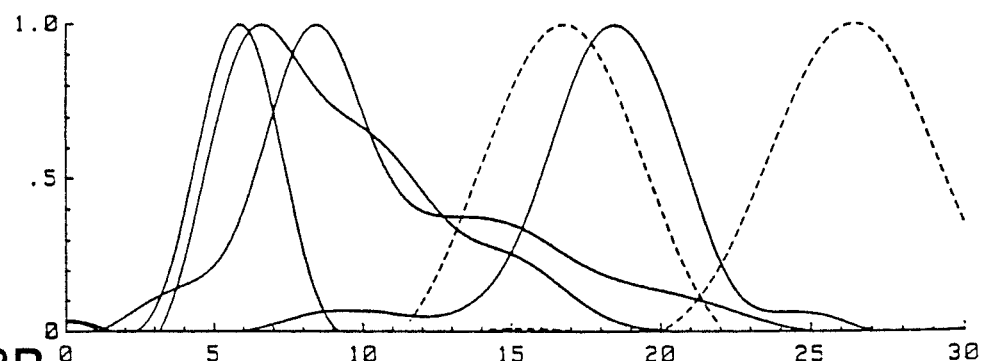
Figure 2B:
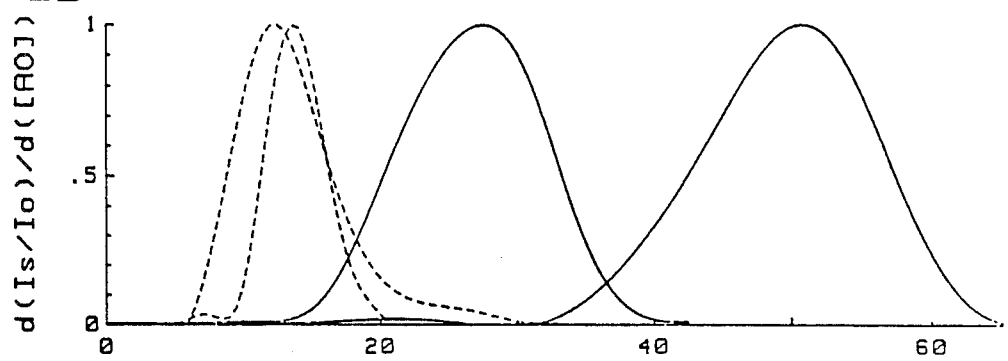

FIGS. 2A and 2B present the titration curves of several homoribo- and homodeoxyribopolymers as well as natural RNA and DNA with acridine orange (AO). The experiments were made as described in Example 1 except that 0.1% Triton X-100 was included in the buffer. As is evident, the condensation of homoribopolymers occurs at lower-liquid concentration as compared with homodeoxyribopolymers (e.g., poly(rA) vs poly(dA) and poly(rU) vs poly(dU), FIG. 2A). Likewise, condensation of natural RNAs takes place at lower AO concentration than that of either native or denatured DNA (FIG. 2B).

Because complexes of AO with ss nucleic acids exhibit red luminescence it is possible to monitor the collapse of the polymers using luminescence measurements (e.g., at 650 μm). The transition profiles when measured by luminescence changes are shifted to lower free-ligand concentrations as compared with the transition profiles monitored by light-scatter measurements (Kapuscinski and Darzynkiewicz, supra).

EXAMPLE 3

Identification of Nucleic Acids Based on Differences in Base Composition

The experiments as described in Examples 1 and 2 can be used to prepare a library of transition curves using different ligands and different synthetic and natural nucleic acids. As explained in the text the critical free-ligand concentration ($L_c$) can be used to characterize the different polymers. $L_c = L_m - L_b$ where: $L_m$ is the total ligand concentration at the midpoint of transition (e.g., determined by one half of the numerically integrated area under the derivative curve of the transition), $L_b$ is the bound-ligand concentration at the midpoint; for ss polymers and AO or DHAQ, $L_b = 0.5$ P (P = concentration of the polymer expressed as moles of phosphates/l). For polymers with 100% double strandness, $L_b = 0.58$ P because part of the ligand is bound by intercalation to the ds portion of the polymer. Note that $L_c$ is independent of the polymer concentration. Thus, the $L_c$ value can be used to identify particular types of nucleic acids.

Table I lists $L_c$ values for AO and DHAQ of several ss and ds polymers:

TABLE 1

| | Critical free-ligand concentration ($L_c$) μM | |
|---|---|---|
| Polymer[a] | AO | DHAQ |
| Single stranded: | | |
| poly(dC) | 5.4 | 0.8 |
| poly(dA) | 13.6 | 3.4 |
| poly(dI) | 17.3 | <0.1 |
| poly(dT) | 23.4 | 2.1 |
| Double stranded: | | |
| poly(dI) · poly(dC) | 14.7 | 2.7 |
| poly(dI—dC) · poly(dI—dC) | 42.2 | 39.5 |
| poly(dA) · poly(dT) | 29.3 | 3.2 |
| poly(dA—dT) · poly(dA—dT) | 62.3 | 26.5 |
| calf thymus DNA | 51.2 | 14.7 |

[a]Titration of the polymers with DHAQ or AO was performed as described in Example 1 or 2, respectively; 0.1% Triton X-100 was present in all experiments.

Additionally, FIG. 2A illustrates the usefulness of the proposed method to differentiate between the homoribopolymers differing in primary structure.

EXAMPLE 4

Analysis of the Secondary Structure of Nucleic Acids

Figure 2C:
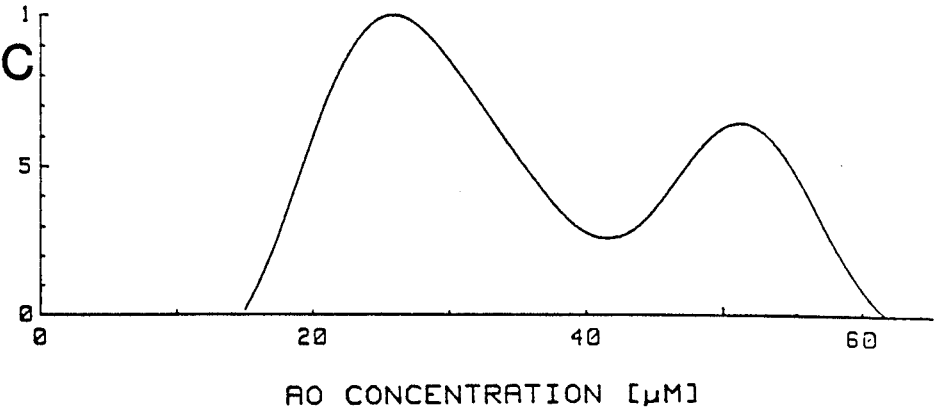

Table I (Example 3) lists $L_c$ values of ss- and ds-deoxyribopolymers. It is evident that most ds polymers have higher $L_c$ values than ss nucleic acids. FIGS. 2B and 2C also illustrate discrimination between the native and denatured form of calf thymus DNA.

EXAMPLE 5

Estimation of the Molecular Weight of Nucleic Acids

In the experiment presented in FIG. 2C concentrations (calculated per monomer) of native and denatured DNA were similar. However, the area S, representing transition of the native DNA is only one half of that of the denatured DNA. This difference, in all probability, is due to the strand separation during the thermal denaturation; namely, the intensity of the scattered light in solution is proportional to the number of scatterers. Thus, at the same concentration (of monomer) there are twice as many scatterers in the solution of denatured nucleic acid in comparison with its native form. The ligand-induced collapse of nucleic acids, therefore, can be used to estimate molecular weight of the polymers if appropriate standards are available.

DISCUSSION

Based on our recent studies on interactions between acridine orange and nucleic acids, the model describing binding of the intercalating cations, which explains both the specificity of the ligand binding in relation to the primary structure of nucleic acids and precipitation of the product, was proposed (Kapuscinski et al, (1982), Kapuscinski et al, (1981), Darzynkiewicz et al, (1983), Kapuscinski et al (1983), Kapuscinski and Darzynkiewicz (1983), all supra). According to this model the initial attachment of the ligand (nucleation) via partial insertion of the planar aromatic ring between adjacent bases of the single-stranded polymer ("partial intercalation") is followed by the cooperative process which also involves ligand-base interactions. Namely, from the nucleation point outwards, the partial intercalation progresses and thus the stacks of the alternating sequence (ligand-base) are formed along the nucleic acid molecule. As a result of such binding of the cation, a charge-neutralization of the nucleic acid takes place, which leads to its condensation. Agglomeration of the condensed forms and appearance of the visible precipitate are the final steps of the reaction.

In the case of the double-stranded nucleic acid, its denaturation precedes condensation. The denaturation is induced by the ligands via a mechanism discussed by us in recent publications. The mechanism, in principle, is similar to that operating for single-stranded nucleic acids, i.e., it involves partial intercalation of the ligand to single-stranded regions (e.g., available during "breathing" of the polymers), cooperative progression of the binding, destruction of the double-stranded structure ("melting") and condensation. Thus, the transition of double-stranded nucleic acids as measured by light scatter, occurs at higher concentration of the ligand in comparison with single-stranded polymer of the same type, because the denaturation step is involved. This explains the discrimination of single-stranded vs double-stranded nucleic acids by the method proposed by us. Discrimination of nucleic acids based on their primary structure (base- or sugar-composition) is a consequence of different affinities of the ligand to the single-stranded forms which involves both the nucleation and the cooperativity process.

It will be understood that the specification and examples are illustrative but not limitative of the present invention and that other embodiments within the spirit and scope of the invention will suggest themselves to those skilled in the art.

What is claimed is:

1. A method for separately recovering nucleic acids present in a sample containing a mixture of nucleic acids based upon the primary or secondary structure, or both, of the nucleic acids, comprising the steps of:
   treating the sample with an aqueous solvent to dissolve the nucleic acids present in the mixture;
   contacting the resulting sample containing dissolved nucleic acids with increasing concentrations of a 3- or 4-ring aromatic cationic ligand, which binds to single-stranded nucleic acids by cooperative association and induce condensation thereof, so as to form a series of precipitates;
   monitoring the formation of the precipitates so as to obtain a series of transition curves;
   separating each of the precipitates from the aqueous solvent using the transition curves so as to obtain a precipitated fraction for each nucleic acid present in the sample;
   renaturing each precipitated fraction; and
   separately recovering from each fraction the nucleic acid present therein.

2. The method of claim 1 wherein the cationic ligand is AO or DHAQ.

3. The method of claim 1, wherein renaturing each precipitated fraction and separately recovering from each fraction the nucleic acid present therein comprises dissolving each fraction in an organic solvent and removing the ligand by contact with a cation exchange resin.

4. A method for detecting the presence of a nucleic acid of interest in a sample containing a mixture of nucleic acids based upon the primary or secondary structure, or both, of the nucleic acid of interest, comprising the steps of:
   treating the sample with an aqueous solvent to dissolve the nucleic acids present in the mixture;
   contacting the resulting sample containing dissolved nucleic acids with increasing concentrations of a 3- or 4-ring aromatic cationic ligand, which binds to single-stranded nucleic acids by cooperative association and induces condensation thereof, so as to form a series of nucleic acid-ligand particles;
   monitoring the formation of the nucleic acid-ligand particles so as to obtain a series of transition curves; and
   detecting the presence of the nucleic acid of interest by correlating the series of transition curves with the primary or secondary structure, or both, of the nucleic acid of interest.

5. A method for quantitatively determining the amount of a nucleic acid of interest present in a sample containing a mixture of nucleic acids based upon the primary or secondary structure, or both, of the nucleic acid of interest, comprising the steps of:
   treating the sample with an aqueous solvent to dissolve the nucleic acids present in the mixture;
   contacting the resulting sample containing dissolved nucleic acids with increasing concentrations of a 3- or 4-ring aromatic cationic ligand, which binds to single-stranded nucleic acids by cooperative association and induces condensation thereof, so as to form a series of nucleic acid-ligand particles;
   monitoring the formation of the nucleic acid-ligand particles so as to obtain a series of transition curves; and
   detecting the amount of the nucleic acid of interest by correlating the series of transition curves with the primary or secondary structure, or both, of the nucleic acid of interest.

* * * * *